United States Patent [19]
Perkins et al.

[11] Patent Number: 5,681,274
[45] Date of Patent: Oct. 28, 1997

[54] VARIABLE LENGTH URETHERAL STENT

[75] Inventors: D. H. Perkins; Linda D. Elbert, both of Bloomington, Ind.; Douglas E. Godshall, Marlboro, Mass.; Clifford L. Smith, Bloomington, Ind.

[73] Assignee: Boston Scientific Corporation, Natick, Mass.

[21] Appl. No.: 414,649

[22] Filed: Mar. 31, 1995

[51] Int. Cl.⁶ .................................................. A61M 37/00
[52] U.S. Cl. ...................... 604/8; 604/264; 604/280; 604/281
[58] Field of Search .................... 604/8, 9, 93, 164, 604/280, 281, 264; 623/1, 12; 606/191, 108, 197

[56] References Cited

U.S. PATENT DOCUMENTS

| | | | |
|---|---|---|---|
| 4,531,933 | 7/1985 | Norton et al. | 604/8 |
| 4,610,657 | 9/1986 | Densow | 604/8 |
| 4,643,716 | 2/1987 | Drach | 604/8 |
| 4,787,884 | 11/1988 | Goldberg | 604/8 |
| 4,790,810 | 12/1988 | Pugh, Jr. et al. | 604/8 |
| 4,913,683 | 4/1990 | Gregory | 604/8 |
| 4,931,037 | 6/1990 | Wetterman | 604/8 |
| 4,935,004 | 6/1990 | Cruz | 604/281 |
| 4,950,228 | 8/1990 | Knapp, Jr. et al. | 604/8 |
| 5,364,340 | 11/1994 | Coll | 604/8 |
| 5,380,298 | 1/1995 | Zabetakis et al. | 604/280 |
| 5,407,432 | 4/1995 | Solar | 604/164 |

Primary Examiner—John G. Weiss
Assistant Examiner—Bruce E. Snow
Attorney, Agent, or Firm—Pearson & Pearson

[57] ABSTRACT

A variable length ureteral stent assembly. A central catheter tube forms a ureter stent with a retention structure for anchoring the stent in the ureter particularly within the bladder and kidney. The catheter tube is formed of a shape memory material and at least one of the retention structures includes a end portion of the catheter wrapped spirally into a multiple-turn planar coil having an axis that is transverse to the plane of the structure. The retention structure can then be partially unwound while still providing an anchoring function. Partially unwinding increases the length of an intermediate section of the ureteral stent.

20 Claims, 3 Drawing Sheets

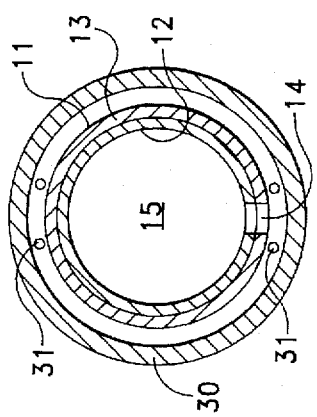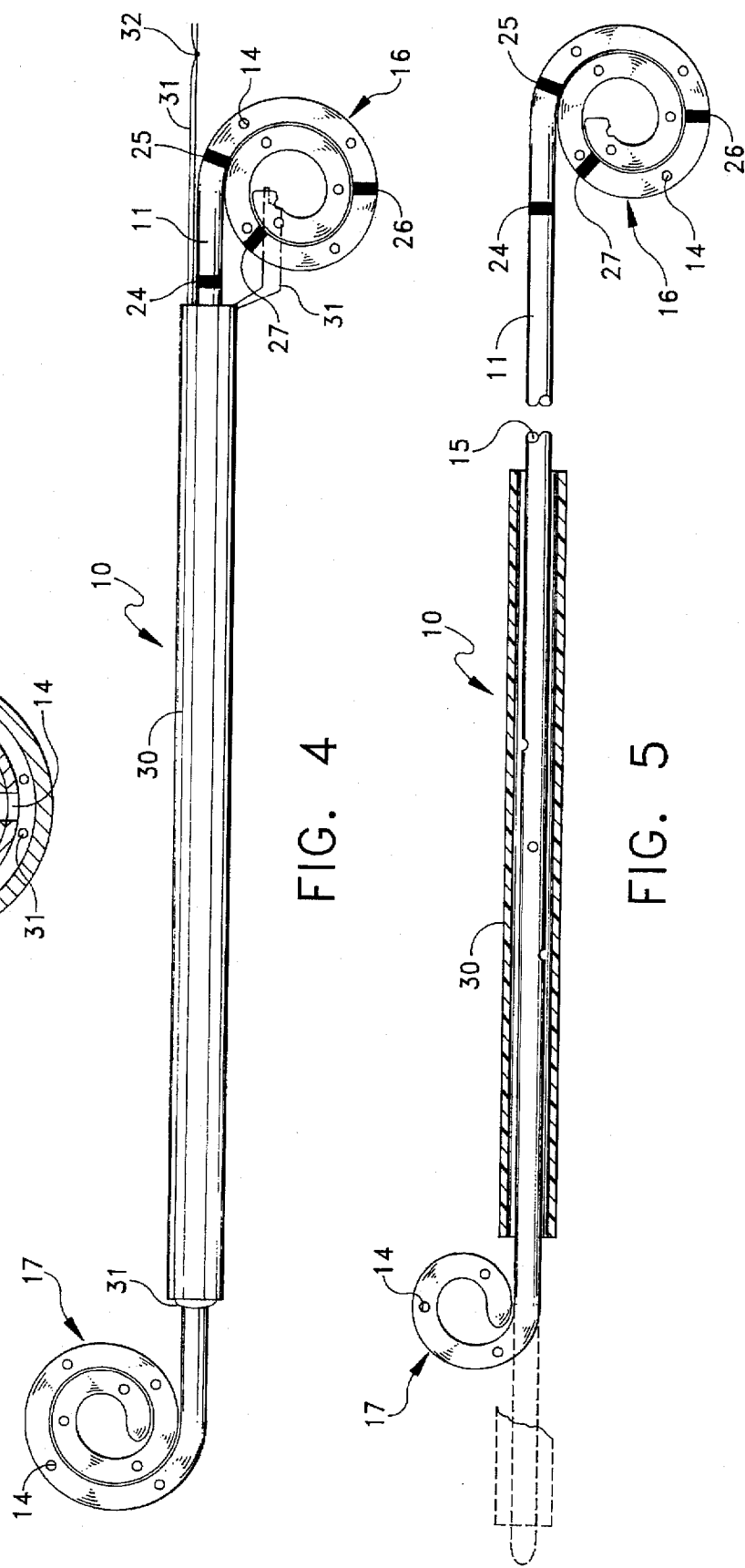

5,681,274

VARIABLE LENGTH URETHERAL STENT

BACKGROUND OF THE INVENTION

1. Field of the Invention

This invention generally relates to medical prostheses and particularly to variable length ureteral stents.

2. Description of Related Art

Ureteral stents are well known and widely accepted as viable prostheses for bypassing ureteral obstructions and promoting drainage by acting as a drainage tube between the kidneys or renal pelvis and the bladder. U.S. Pat. No. 4,950,228 to Knapp, Jr. et al. discloses one such ureteral stent that includes a tubular member of substantially uniform outside diameter with integral bladder and kidney retention structures. The bladder retention structure comprises an end portion of the tube formed in a retention, or J, curve to retain that end in the bladder. The other end has three portions with a first portion extending from the stent body and being substantially straight, a second portion extending from the first portion and being in the shape of a 360° helical curve and a third portion extending from the second portion and terminating at a distal tip. The resulting structure anchors the stent in the renal pelvis.

As the use of such ureteral stents has continued, it has been found that various applications require stents of different diameters. Moreover, differences in individual anatomies require stents having different effective lengths between the end retention structures, such as the curved and helical coil portions located at the bladder and kidney ends of the stent as shown in the Knapp, Jr. et al. patent. Consequently hospitals and other facilities inventory stents of different diameters and for each diameter, stents of different lengths, typically six stents of different lengths for each diameter.

Generally a physician must estimate ureter length before beginning a procedure. If the estimate is near the end of a particular length range, it is possible to select a stent that is slightly too long or too short. However, that fact can not be determined until the stent has been implanted. The procedure for correcting any incorrect selection involves removing that stent and placing a longer or shorter stent in the ureter thereby complicating the procedure and potentially increasing patient trauma.

U.S. Pat. No. 4,531,933 to Norton et al. discloses a ureteral stent of variable length including an elongated flexible silicon tubular member having a series of helical coils at each end. In this structure the helical coils lie along an axis generally parallel to and offset from the axis of a center section. The bladder retention structure includes a multi-turn helical coil. A physician varies stent length by straightening successive coils forming the bladder retention structure, provided at least one full turn of the helical coil remains.

In U.S. Pat. No. 4,643,716 to Drach a bladder retention structure includes a serpentine planar extension of the tubular member. Individual sections of the serpentine extension can be straightened to extend the effective length of the stent.

Although the stents disclosed in the Norton et al. and Drach patents can reduce inventory requirements, each retention structure located in the bladder has a larger volume than the retention structures such as disclosed in the Knapp, Jr. et al. patent. This excess volume of this structure, that is a foreign body, increases a risk of tissue irritation. To minimize the potential for irritation, physicians often clip any excess length of the retention structure to minimize its volume in the bladder. It has also been found that the stents of this type can be more difficult to implant and remove because the retention structure does not facilitate straightening in the body.

SUMMARY

Therefore it is an object of this invention to provide an improved variable length ureteral stent.

Another object of this invention is to provide a variable length ureteral stent in which a retention structure occupies a minimal volume.

Still another object of this invention is to provide a variable length stent that minimizes the potential for tissue irritation.

Yet another object of this invention is to provide a ureteral stent that facilitates implantation and removal and that eliminates the need for any clipping of a retention structure.

Still yet another object of this invention is to provide a variable length ureteral stent that minimizes the time required for implantation and removal and that reduces the potential for patient trauma during such procedures.

Yet still another object of this invention is to provide a variable length ureteral stent that minimizes inventory requirements.

In accordance with this invention a ureteral stent comprises an elongated flexible tubular member with drainage means extending along the length thereof. Either or both ends of the ureteral stent terminate with a multiple-turn, planar coil retention structure formed with multiple turns wound upon each other within the same plane for anchoring that end of the ureteral stent in the body.

In accordance with another aspect of this invention a ureteral stent comprises an elongated, flexible tubular member provided with drainage means extending along the length thereof with a retention structure at either end for anchoring the ureteral stent in a patient's bladder and kidney or renal pelvis. A straightening tube overlies the tubular member for straightening the retention structures, at least one of which includes a multiple-turn, planar coil formed by the tubular member formed with multiple turns wound upon each other within the same plane.

BRIEF DESCRIPTION OF THE DRAWINGS

The appended claims particularly point out and distinctly claim the subject matter of this invention. The various objects, advantages and novel features of this invention will be more fully apparent from a reading of the following detailed description in conjunction with the accompanying drawings in which like reference numerals refer to like parts, and in which:

FIG. 3 is an enlarged cross-sectional view taken along lines 3—3 in FIG. 1;

FIG. 4 depicts a ureteral stent constructed in accordance with this invention as it is ready for use;

FIG. 5 depicts the use of a straightener shown in FIGS. 1 and 3; and

DESCRIPTION OF ILLUSTRATIVE EMBODIMENTS

Figure 1:
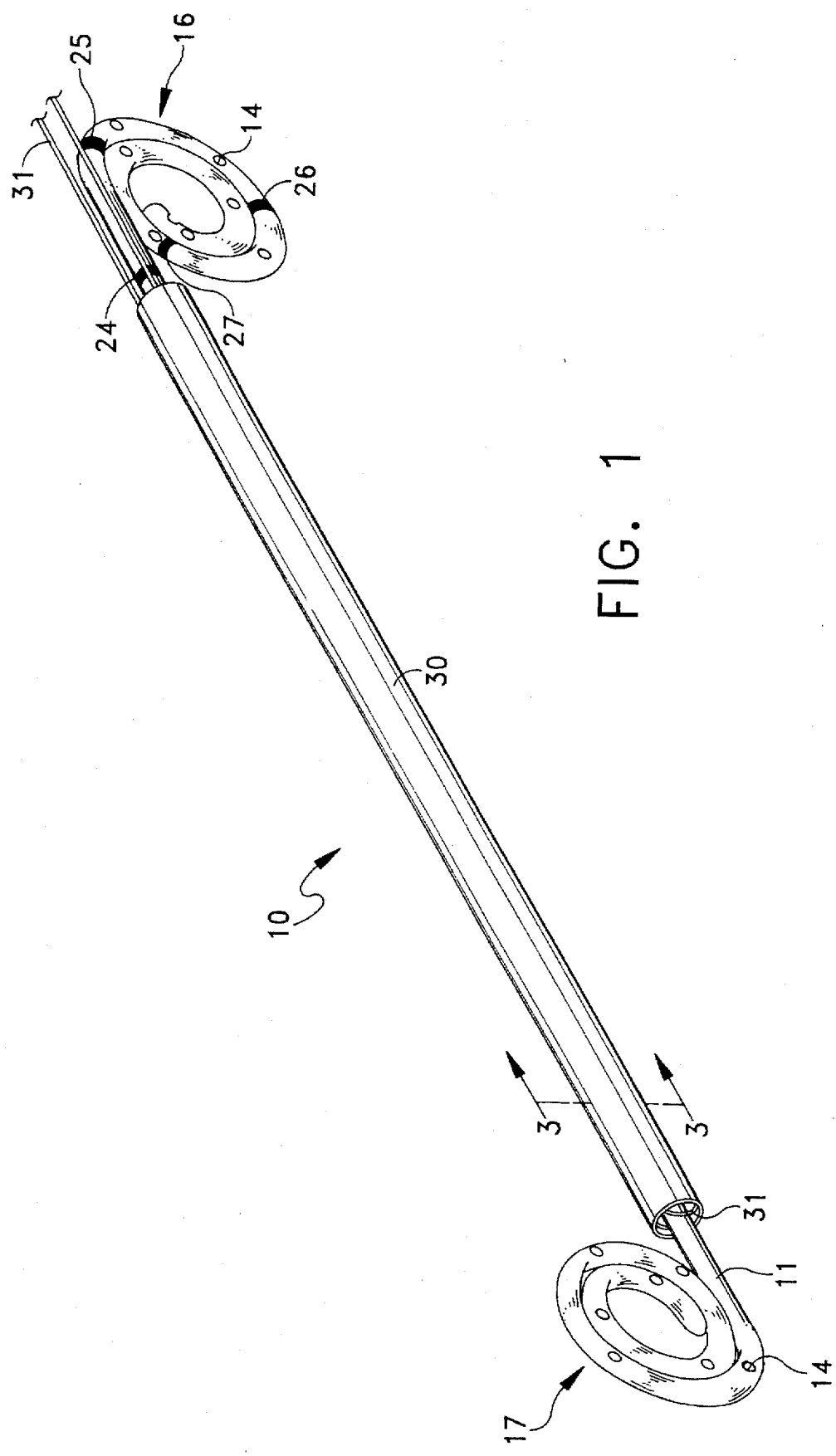
FIG. 1 is a perspective view of the ureteral stent assembly constructed in accordance with this invention.

In the following discussion like numerals refer to like elements throughout. In addition the ends of a ureteral stent assembly 10 such as shown in FIG. 1, are referred to as the "bladder" and "kidney" ends respectively. The "kidney" end of the ureteral stent assembly 10 is meant to denote the end implanted in the kidney or renal pelvis. As disclosed, the ureteral stent assembly 10 includes a tubular catheter or ureteral stent 11. As shown in FIG. 3, the ureteral stent 11 includes a central tube or catheter 12 formed of a biocompatible shape memory tubing, such as Percuflex® tubing. In a preferred embodiment, the catheter 12 includes a thin exterior lubricous coating 13 to facilitate the placement of the ureteral stent 11. The interior surface of the catheter 12 could also be coated with a lubricous coating. The relative thickness of the catheter 12 and coating 13 are obviously not to scale in FIG. 3; the thickness of the coating is exaggerated for purposes of explanation. The ureteral stent 11 also includes drainage holes 14 formed through the catheter 12 and coating 13 at various locations thereby to admit urine or other fluids into a lumen 15 for transport to the bladder past any obstruction in the ureter.

Figure 2:
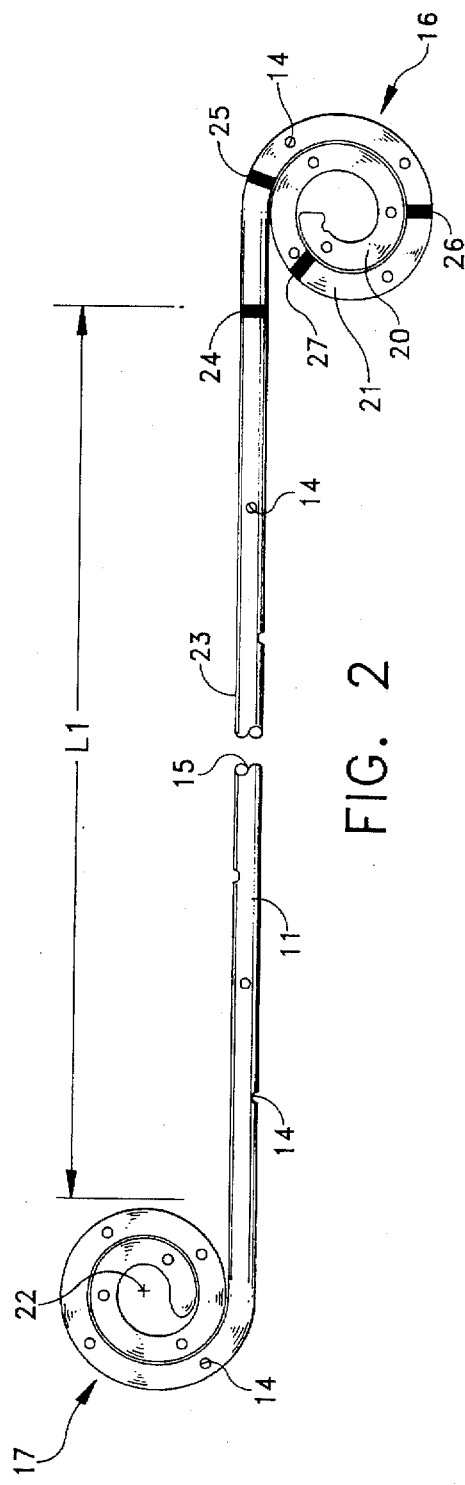
FIG. 2 is a plan view of a ureteral stent constructed in accordance with this invention that is useful in the assembly shown in FIG. 1.

Referring now to FIG. 2, the ureteral stent 11 includes a bladder retention structure 16 and a kidney retention structure 17 formed by bending the ends of the tubular catheter 12 into a planar spiral. More specifically, each of the structures 16 and 17 is formed by shaping the end portions of the ureteral stent 11 into a multiple turn, spiral planar coil formed with multiple turns wound upon each other within the same plane. For example, the bladder retention structure 16 includes an inner turn 20 and outer turn 21 thereby to form a two-turn spiral, planar coil.

Both retention structures 16 and 17 have the same construction as shown. In a preferred embodiment each structure forms the spiral about an axis, such as an axis 22 for the structure 17, that is transverse to and offset from an intermediate portion 23 of the ureteral stent 11. Thus, the spiral multi-turn coils forming the structures 16 and 17 are offset from the axis of the intermediate portion 23 and lead tangentially into the intermediate portion 23 on opposite sides. Moreover, as is most clearly shown in FIG. 1, the retention structures 16 and 17 lie in a single plane that is common with the intermediate portion 23 and extend oppositely from the intermediate portion 23. That is, the structure 16 depends from the intermediate portion 23 in the orientation of FIG. 1 while the structure 17 extends upwardly.

Conventionally a physician positions a ureteral stent through an endoscopic device so the physician can visualize the area proximate the bladder retention structure 16. In accordance with another aspect of this invention, a series of visual markers 24, 25, 26 and 27 spaced along the portion of the ureteral stent 11 that forms the bladder retention structure 16. The markers 24 through 27 enable the physician to determine the extent to which the coil in that retention structure 16 unwraps and assure that at least one full coil turn remains within the patient's bladder. As will be apparent, the markers 24 through 27 could also be radiopaque to enhance the radiographic positioning.

FIGS. 1 and 4 depict the form of an ureteral stent assembly 10 including the ureteral stent 11 constructed in accordance with this invention that also includes a straightening tube 30 and sutures 31.

The straightening tube 30 facilitates the installation of the ureteral stent 11 on a guidewire. In use the physician initially displaces the straightening tube 30 toward the kidney retention structure 17 causing it to straighten as shown in FIG. 5 wherein the straightening tube 30 has advanced to unwind one turn. Eventually the physician displaces the straightening tube 30 to a position 33 as shown in phantom in FIG. 5 thereby to completely straighten the ureteral stent 11 and enable the insertion of a guidewire through the lumen 15.

After the physician advances the guidewire through the lumen 15 to the bladder retention structure 16, the physician slides the straightening sleeve 30 to the right in the figures. The guidewire has sufficient stiffness that the kidney retention structure cannot reform. Moving the straightening tube 30 fully to the right unwinds the coils in the bladder retention structure 16 thereby to allow the guidewire to pass fully through the ureteral stent 11. At this point the straightening tube 30 can be easily removed by continued displacement to the right. After removing the straightening tube 30, the ureteral stent 11 is mounted on the guidewire ready for insertion.

Sutures 31 connect to the tip of the ureteral stent 11 at the bladder retention structure 16. In this particular embodiment the sutures 31 could extend through the all or a portion of the straightening tube 30 intermediate the ureteral stent 11 and then loop back to a free end 32. The sutures are also shown in FIG. 3 intermediate the straightening tube 30 and the ureteral stent 11. Removal of the straightening tube obviously frees the sutures. The use of sutures 31 is well known in the art.

During placement, the physician determines the required length of the intermediate portion 23 between the retention structures 16 and 17 that corresponds to the length of the patient's ureter. This determines the number of markers 24 through 27 that should lie in the straightened intermediate portion 23. The appearance of four markers in a straight section indicates full extension with only a single full turn to be formed when the guidewire is removed and internal stresses cause the free end of the ureter stent 11 to form into the original coil. As will also be apparent, the forces that cause the straightened ends of the catheter tubing 12 to wrap back into the coils will be limited so that they are overcome when the retention structures abut surrounding tissue.

Figure 6:
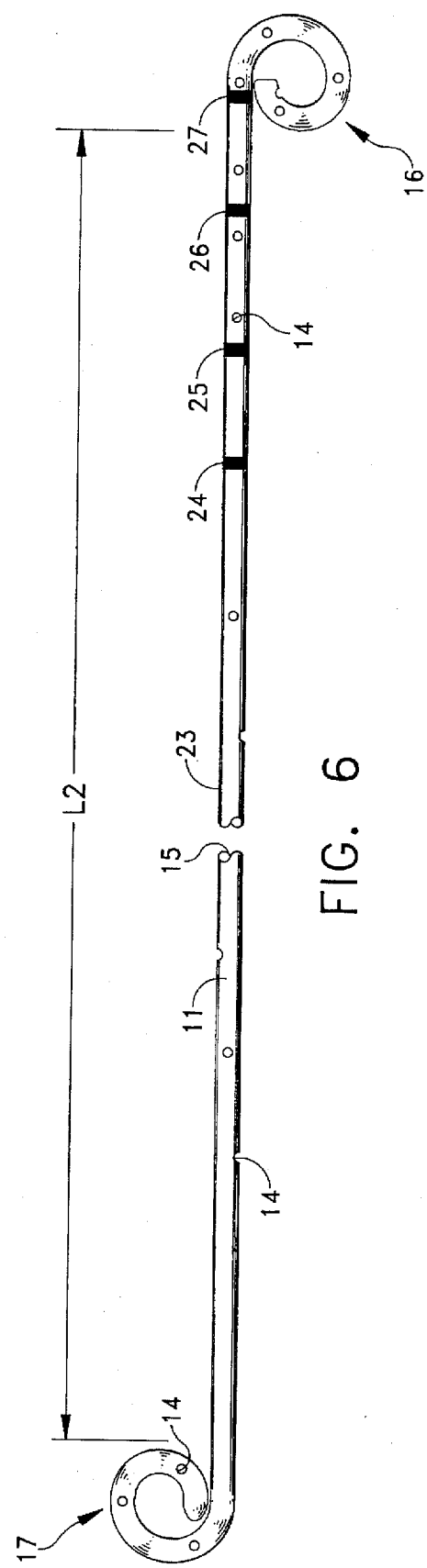
FIG. 6 depicts the stent in FIG. 1 in a fully extended configuration.

FIG. 6 discloses the ureteral stent 11 in a fully extended configuration in which each of the bladder and kidney retention structures 16 and 17 have their smallest configuration comprising slightly over one complete turn. In one particular embodiment the distance between the retention structures 16 and 17 shown in FIG. 1 is about 22 cm.; in FIG. 6 that distance increases to about 30 cm. Thus as will be apparent, a single ureteral stent 11 constructed in accordance with this invention has infinite variation in length over a range that exceeds the range ureter length occurring as a result of anatomical differences. Thus, it is only necessary to inventory one ureteral stent assembly for each lumen size in order to accommodate the various ureteral lengths of the patient population. The structure shown in FIG. 1 allows each of the retention structures 16 and 17 to include at least one complete turn for residing in the bladder and in the kidney. However, for shorter ureteral lengths all the coils reside in either the bladder or the kidney. The planar nature of the multi-turn coils however, produces a overall size of the retention structure that remains basically the same as prior art single-turn retention coils. Consequently there is no requirement that a physician clip or cut off any excess retention coil materials as in prior art variable length stents. The compact nature of the variable length retention structures minimizes the potential for tissue irritation, so such clipping is not necessary. Consequently this invention eliminates what can otherwise be a time consuming and complex step.

The location of the planar retention structures in a common plane with the coils wrapped about axes normal to a plane facilitate straightening the coils in a direction parallel to and in line with the intermediate section 23. The use of a lubricous coating 13 shown in FIG. 3 facilitates transport through the ureter and minimizes any tendency of materials to encrust the exterior surface of the ureteral stent 11. An interior lubricous coating will facilitate transport over a guidewire. The markings 25 through 27 facilitate the positioning of the stent. The embodiments including an integral straightener 30 facilitate the loading and subsequent placement of the ureteral stent 11 on a guidewire.

Consequently the ureteral stent 11 constructed in accordance with this invention attains all the objectives of this invention. Moreover it will be apparent that other embodiments may exist that meet some or all of these objectives. For example, one or the other of the multiple-turn retention coils could be replaced by another retention structure such as a conventional single-turn or J-curved retention structure. As specifically disclosed that the retention coils have a two-turn configuration, additional turns might be utilized to provide further extensions. The visual markings 24 through 27 can be included or omitted from a particular embodiment. Similarly the ureteral stent 11 may be supplied with or without a straightener 30. Therefore, it is the intent of the appended claims to cover all such variations and modifications as come within the true spirit and scope of this invention.

What is claimed as new and desired to be secured by Letters Patent of the United States is:

1. An ureteral stent comprising an elongated flexible tubular member provided with drainage means extending along the length thereof, said tubular member forming first and second retention coil means at opposite ends of an intermediate portion of said tubular member, each of said retention coil means being formed with multiple turns wound upon each other within the same plane and said first and second retention coil means and said intermediate portion lying in a single plane thereby to provide anchors for said ureteral stent in the body.

2. An ureteral stent as recited in claim 1 wherein each of said retention coil means is wound about a coil axis that is transverse to the single plane.

3. An ureteral stent as recited in claim 2 wherein said first and second retention coil means lie on opposite sides of said intermediate portion.

4. An ureteral stent as recited in claim 3 wherein said intermediate portion extends along a second axis and the coil axis of each of said retention coil means is offset from the second axis.

5. An ureteral stent as recited in claim 3 wherein said intermediate portion extends along a second axis and the coil axis of each of said retention coil means is perpendicular to the second axis.

6. An ureteral stent as recited in claim 3 wherein said intermediate portion extends along a second axis and the coil axis of each of said retention coil means is perpendicular to and offset from the second axis.

7. An ureteral stent comprising an elongated flexible tubular member provided with drainage means extending along the length thereof, said tubular member forming a retention coil at each end thereof formed with multiple turns wound upon each other within the same plane at each end of said tubular member for anchoring said ureteral stent in the body, each of said retention coils lying in a single plane.

8. An ureteral stent as recited in claim 7 wherein each of said coils is wound about a coil axis that is transverse to the single plane.

9. An ureteral stent as recited in claim 7 wherein said tubular member extends along a second axis intermediate the ends and the coil axis of each of said coils is offset from the second axis.

10. An ureteral stent as recited in claim 7 wherein said tubular member extends along a second axis intermediate the ends and the coil axis of each of said coils is perpendicular to the second axis.

11. An ureteral stent as recited in claim 7 wherein said tubular member extends along a second axis intermediate the ends and the coil axis of each of said coils is perpendicular to and offset from the second axis.

12. An ureteral stent as recited in claim 7 wherein said tubular member is formed of a shape memory material.

13. An ureteral stent as recited in claim 7 wherein said tubular member is formed of a shape memory material having a lubricous coating.

14. An ureteral stent as recited in claim 7 adapted for placement through an endoscopic device wherein the portion of said tubular member forming one of said retention coils additionally comprises spaced markers thereon.

15. A ureteral stent assembly comprising:
(A) a ureteral stent having an elongated flexible tubular member provided with drainage means extending along the length thereof, said tubular member having a retention coil means at each end thereof, said retention coil means at each end thereof being formed with multiple turns wound upon each other within the same plane for anchoring said ureteral stent in the body and having an axially extending intermediate portion between said retention coil means, each of said retention coil means and said intermediate portion lying in a single plane, and
(B) straightener means coaxial with and slidable with respect to said intermediate portion toward one of said retention coil means thereby to straighten the portion of the tubular member forming said one retention coil means.

16. An ureteral stent as recited in claim 15 wherein said tubular member is formed of a shape memory material having a lubricous coating.

17. An ureteral stent as recited in claim 15 adapted for placement through an endoscopic device wherein the portion of said tubular member forming one of said retention coil means additionally comprises spaced markers.

18. An ureteral stent as recited in claim 15 wherein said retention coil means are formed to extend oppositely from said intermediate portion of said tubular member, the axis of each of said retention coil means being perpendicular to and offset from the second axis and each of said retention coil means being tangential to the proximate intermediate section.

19. A ureteral stent assembly for being implanted through an endoscopic device in the ureter intermediate the bladder and kidney, said assembly comprising:
(A) a ureteral stent having an elongated flexible tubular member formed of a shape member material having a lubricous coating and provided with drainage means extending along the length thereof, said tubular member having at each end thereof a retention coil means formed with multiple turns wound upon each other within the same plane and about an axis for anchoring said ureteral stent in the body and forming an axially extending intermediate portion between said retention coil means, each of said retention coil means and said intermediate portion lying substantially in a single plane and said retention coil means axes being parallel and being normal to said single plane,
(B) straightener means coaxial with and slidable with respect to said intermediate portion toward one said retention coil means thereby to straighten that portion of the tubular member forming the retention coil means, and (C) spaced markers formed on a portion of said tubular member forming one of said retention coil means.

20. An ureteral stent as recited in claim 19 additionally comprising a suture attached to the end of said tubular member at the marked retention coil means.

* * * * *